(12) United States Patent
Li et al.

(10) Patent No.: US 10,583,300 B2
(45) Date of Patent: Mar. 10, 2020

(54) LEADLESS IMPLANTABLE MEDICAL DEVICE WITH FIXATION ANTENNA MEMBER

(71) Applicant: PACESETTER, INC., Sylmar, CA (US)

(72) Inventors: Perry Li, Temple City, CA (US); Brett Villavicencio, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 15/661,916

(22) Filed: Jul. 27, 2017

(65) Prior Publication Data

US 2019/0030346 A1    Jan. 31, 2019

(51) Int. Cl.
| | |
|---|---|
| *A61N 1/37* | (2006.01) |
| *A61N 1/372* | (2006.01) |
| *A61N 1/375* | (2006.01) |

(52) U.S. Cl.
CPC ....... *A61N 1/37229* (2013.01); *A61N 1/3702* (2013.01); *A61N 1/3756* (2013.01); *A61N 1/37518* (2017.08); *A61N 1/3754* (2013.01); *A61N 1/37512* (2017.08)

(58) Field of Classification Search
CPC .... A61B 5/07; A61B 5/68; A61N 1/08; A61N 1/35; A61N 1/36; A61N 1/37
See application file for complete search history.

(56) References Cited

U.S. PATENT DOCUMENTS

| | | | |
|---|---|---|---|
| 7,295,879 B2 | 11/2007 | Denker et al. | |
| 8,939,905 B2 | 1/2015 | Schugt et al. | |
| 9,265,436 B2 | 2/2016 | Min et al. | |
| 2005/0080346 A1 | 4/2005 | Gianchandani et al. | |
| 2010/0179449 A1 | 7/2010 | Chow et al. | |
| 2013/0085350 A1 | 4/2013 | Schugt et al. | |
| 2016/0059010 A1* | 3/2016 | Sharma | A61N 1/36007 607/40 |
| 2016/0121128 A1* | 5/2016 | Fishler | A61N 1/3622 607/14 |

FOREIGN PATENT DOCUMENTS

WO    2012016157 A1    2/2012

* cited by examiner

*Primary Examiner* — Ankit D Tejani (57) ABSTRACT

Devices and methods are provided for a leadless implantable medical device (LIMD) comprising a housing. An electrode is disposed on the housing. An electronics circuit is disposed in the housing and is configured to sense cardiac signals, and/or generate and deliver pacing signals to the electrode. A transceiver circuit is disposed in the housing, and is configured to communicate wirelessly with an external device. A fixation antenna electrically separate from the electrode is disposed on a distal portion of the housing and is electrically coupled to the transceiver circuit, and configured to operate as an antenna for communication between the transceiver circuit and the external device.

9 Claims, 5 Drawing Sheets

LEADLESS IMPLANTABLE MEDICAL DEVICE WITH FIXATION ANTENNA MEMBER

BACKGROUND

Embodiments herein generally relate to implantable medical devices and more particularly, to a leadless cardiac pacemaker with a combined fixation antenna member.

An implantable medical device (IMD) is a medical device that is implanted in a patient to, among other things, monitor electrical activity of a heart, and optionally to deliver therapy, such as a cardiac pacemaker. For cardiac applications, pacemakers are used to deliver pacing pulses to a cardiac chamber to induce a depolarization of that chamber, which is followed by mechanical contraction of that chamber, when a patient's own intrinsic rhythm fails. The IMD further includes sensing circuits that sense electrical activity for the detection of intrinsic cardiac events such as intrinsic atrial depolarizations (detectable as P waves) and intrinsic ventricular depolarizations (detectable as R waves). By monitoring electrical activity, the IMD is able to determine the intrinsic rhythm of the heart and provide stimulation pacing pulses that force atrial and/or ventricular depolarizations at appropriate times in the cardiac cycle to help stabilize the electrical rhythm of the heart.

Some known IMDs utilize one or more electrically-conductive leads that extend from a remotely-located canister or pulse-generator and traverse blood vessels and cardiac chambers to affix connected electrodes to the heart. The housing or canister, referred to as a "can", has electronics and a power source. The can, including the power and processing circuitry, and a portion of the leads are located outside of the patient's heart, and the power and data signals are relayed to and from the heart via the leads. However, the presence of leads may be associated with and/or cause a number of complications.

To mitigate the limitations and complications associated with transvenous leads and the associated IMD, smaller sized devices configured for intra-cardiac implant without the need for transvenous leads have been proposed. These leadless implantable medical devices (LIMD), such as a leadless cardiac pacemaker, are devoid of leads that pass out of the heart to another component, such as a can located outside of the heart. The entire device is configured to be attached to the heart with a fixation antenna, such as a helical member that screws into endocardial tissue. Thus, the power source and the processing circuitry are contained within the device that is attached to the heart. The LIMD includes electrodes that are affixed directly to the can of the device, instead of being separated by a distance traversed by one or more leads. Each LIMD is capable of local pacing and sensing in the chamber of the heart where it is implanted.

Some IMDs communicate with external devices and/or other implanted devices through a radio frequency (RF) antenna. However, the small size of LIMDs create challenges when designing antenna to satisfy the size limitations to fit within the device. Placing an antenna on the exterior of an LIMD also presents challenges. For example, conventional assembly processes for IMDs do not readily permit the addition of external antenna due to an increase in cost and/or assembly time. In addition, an external antenna on the device can interfere with the fixation antenna's ability to hold the LIMD in place.

SUMMARY

In accordance with an embodiment, a leadless implantable medical device is provided comprising a housing. An electrode is disposed on the housing. An electronics circuit is disposed in the housing and configured to sense cardiac signals from the electrode and/or generate and deliver pacing signals to the electrode. A transceiver circuit is disposed in the housing and configured to communicate wirelessly with an external device. A fixation antenna is electrically separate from the electrode and disposed on a distal portion of the housing. The fixation antenna is electrically coupled to the transceiver circuit and configured to operate as an antenna for communication between the transceiver circuit and the external device.

Optionally, the housing includes a feedthrough and the fixation antenna includes a proximal end connected through the feedthrough to the transceiver circuit. The fixation antenna includes a distal end that is electrically open. The fixation antenna is configured to operate as a monopole antenna for communication between the transceiver circuit and the external device. The fixation antenna includes a body that extends between the proximal and distal ends, the body having a length defined based on a wavelength of a carrier frequency for communication with the external device. The length of the body is a quarter multiple of the wavelength of the carrier frequency. The fixation antenna are configured to communicate in accordance with at least one of a MICS protocol, a BLE protocol, a WiFi protocol, or a Bluetooth protocol. The housing is elongated and extends along a longitudinal axis, the fixation antenna is wound in a helix about the longitudinal axis, the fixation antenna formed of a material having a deflection $DEF=LEN_{REST}/LEN_{EXTEND}$ that is no more than 50%, wherein $LEN_{REST}$ represents a rest length of the fixation antenna along the longitudinal axis when in a rest non-extended state, and $LEN_{EXTEND}$ represents an extended length of the fixation antenna along the longitudinal axis when deflected to a fully extended state. The transceiver circuit and fixation are configured to communicate at a frequency of at least one of 400 MHz or 2.4 GHz. The fixation antenna has a diameter between 2.5 mm and 5 mm.

In accordance with embodiments herein, a method for providing an implantable medical device, includes assembling a device housing having electronic circuits therein; connecting a feedthrough assembly to the device housing. An electrode connects to the feedthrough assembly. A fixation antenna connects to the feedthrough assembly, the fixation antenna being configured for operation as an antenna to communicate with an external device. The fixation antenna has a predetermined length to tune the fixation antenna to a communication frequency.

Optionally, the method comprises tuning the fixation antenna to communicate in accordance with at least one of a MICS protocol, Bluetooth protocol, BLE protocol, or WiFi protocol. A length of the fixation antenna is set to be a multiple of a wavelength for a frequency for one of 400 MHz or 2.4 GHz. The fixation antenna is formed of a material having a deflection $DEF=LEN_{REST}/LEN_{EXTEND}$ that is no more than 50%, wherein $LEN_{REST}$ represents a rest length of the fixation antenna along the longitudinal axis when in a rest non-extended state, and $LEN_{EXTEND}$ represents an extended length of the fixation antenna along the longitudinal axis when deflected to a fully extended state.

In accordance with an embodiment a leadless implantable medical device includes a hermetic housing with a pacing electrode disposed on a distal portion of the housing. A fixation antenna is disposed on the distal portion of the housing. The fixation antenna is configured for operation as a monopole antenna to communicate with an external device. An electronics circuit is disposed in the housing and configured to generate and deliver pacing signals to the pacing electrode. A feedthrough assembly operatively connects the fixation antenna to the electronic circuit.

Optionally, the fixation antenna includes a body that extends between a proximal end and the distal end, the body having a length defined based on a wavelength of a carrier frequency for communication with the external device. The length of the body is a quarter multiple of the wavelength of the carrier frequency. The fixation antenna is shaped as a helix with less than five turns of rotation from the distal end to the proximal end. The fixation antenna comprises less than five turns of rotation from the distal end of the fixation antenna to the proximal end of the fixation antenna. The fixation antenna comprises less than one and a quarter turns of rotation from the distal end of the fixation antenna to the proximal end of the fixation antenna. The fixation antenna has a body that is shaped as one of a helix, hook or straight needle. The helix rotates less than or equal to 1800 degrees. The housing is elongated and extends along a longitudinal axis. The fixation antenna is wound in a helix about the longitudinal axis and is formed of a material having a deflection $DEF=LEN_{REST}/LEN_{EXTEND}$ that is no more than 50%, wherein $LEN_{REST}$ represents a rest length of the fixation antenna along the longitudinal axis when in a rest non-extended state, and $LEN_{EXTEND}$ represents an extended length of the fixation antenna along the longitudinal axis when deflected to a fully extended state.

DETAILED DESCRIPTION

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware and circuitry. Thus, for example, one or more of the functional blocks (e.g., processors or memories) may be implemented in a single piece of hardware (e.g., a general purpose signal processor or a block or random access memory, hard disk, or the like). Similarly, the programs may be standalone programs, may be incorporated as subroutines in an operating system, may be functions in an installed imaging software package, and the like. It should be understood that the various embodiments are not limited to the arrangements and instrumentality shown in the drawings.

Embodiments may be implemented in connection with one or more leadless implantable medical devices (LIMDs). For example, the LIMD may represent a cardiac monitoring device, pacemaker, cardioverter, cardiac rhythm management device, defibrillator, neurostimulator, leadless monitoring device, leadless pacemaker and the like. Additionally or alternatively, the LIMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the LIMD may include one or more structural and/or functional aspects of the device(s) described in U.S. Pat. No. 9,232,485 "System And Method For Selectively Communicating With An Implantable Medical Device", which are hereby incorporated by reference.

As used herein, the term "$LEN_{REST}$" represents a rest unloaded length of a fixation antenna as measured along a longitudinal axis when in an original unloaded state with no load applied to the fixation antenna.

The term "$LEN_{EXTEND}$" represents an extended length of the fixation antenna along the longitudinal axis when the fixation antenna is stretched or otherwise deflected to a fully extended state. The fully extended state represents a state of the fixation antenna from which the fixation antenna will return approximately to the rest length when an extension force is released. For example, an extending force may be applied to the fixation antenna to stretch the fixation antenna along the longitudinal axis until reaching the extended length which corresponds to an endurance limit. If the fixation antenna is stretched beyond the endurance limit, elastic properties of the fixation antenna are exceeded which will prevent the fixation antenna from returning to an original unloaded length once the load is released.

The term "leadless" generally refers to an absence of electrically-conductive leads that traverse vessels or other anatomy outside of the intra-cardiac space, while "intra-cardiac" means generally, entirely within the heart and associated vessels, such as the superior vena cava (SVC), inferior vena cava (IVC), coronary sinus (CS), coronary veins (CV), pulmonary arteries, and the like.

Figure 1:
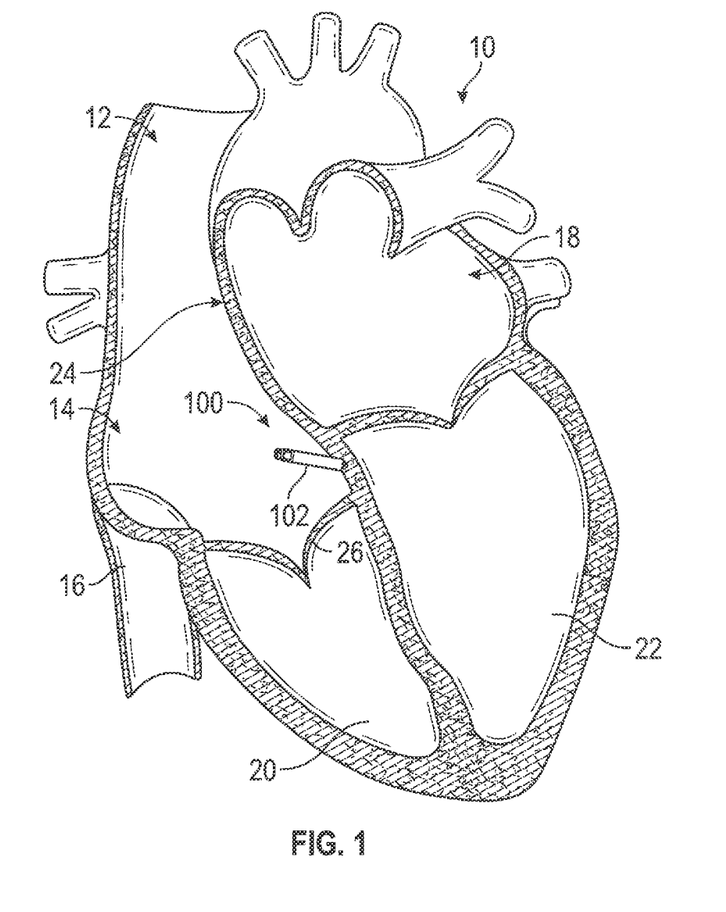
FIG. 1 illustrates a sectional view of a patient's heart with a leadless implantable medical device (LIMD) implanted therein.

FIG. 1 illustrates a sectional view of a patient's heart 10 and shows a leadless implantable medical device (LIMD) 100, such as pacemaker, a cardiac resynchronization device, a cardioverter, a defibrillator, or the like. The LIMD 100 has been placed through the superior vena cava 12 into the right atrium 14 of the heart 10. FIG. 1 also shows the inferior vena cava 16, the left atrium 18, the right ventricle 20, the left ventricle 22, the atrial septum 24 that divides the two atria 14, 18, and a tricuspid valve 26 between the right atrium 14 and the right ventricle 20.

The LIMD 100 comprises a housing 102 configured to be implanted entirely within a single local chamber of the heart 10, such as entirely and solely within the right atrium 14 or the right ventricle 20. Optionally, the LIMD 100 may be implanted entirely and solely within the left atrium 18 or the left ventricle 22, which may require modified implant methods compared to implantation in the right atrium 14 or the right ventricle 20.

As shown in FIG. 1, a local chamber in which the LIMD 100 is implanted is the right ventricle 20. For example, the LIMD 100 is mounted or fixated to the tissue wall of the right ventricle 20 along the septum 24 that divides the right ventricle 20 from the left ventricle 22. The septum 24 wall tissue in the right ventricle 20 may behave physiologically differently than the non-septum ventricular wall tissue. An electrode on the LIMD 100 engages tissue that is part of the conductive network of the right ventricle 20. Optionally, the LIMD 100 is implanted in an area near different regions of tissue that follow the conductive pattern of different chambers of the heart. The LIMD 100 may have another electrode that engages tissue that is part of the conductive network of another chamber, such as the right atrium 14. In other embodiments, the LIMD 100 may be implanted at a different location within the right ventricle 14 or within a different intra-cardiac chamber. Alternatively, multiple LIMDs may be implanted into the patient's heart 10 within different chambers or different segments of the same chamber.

Figure 2:
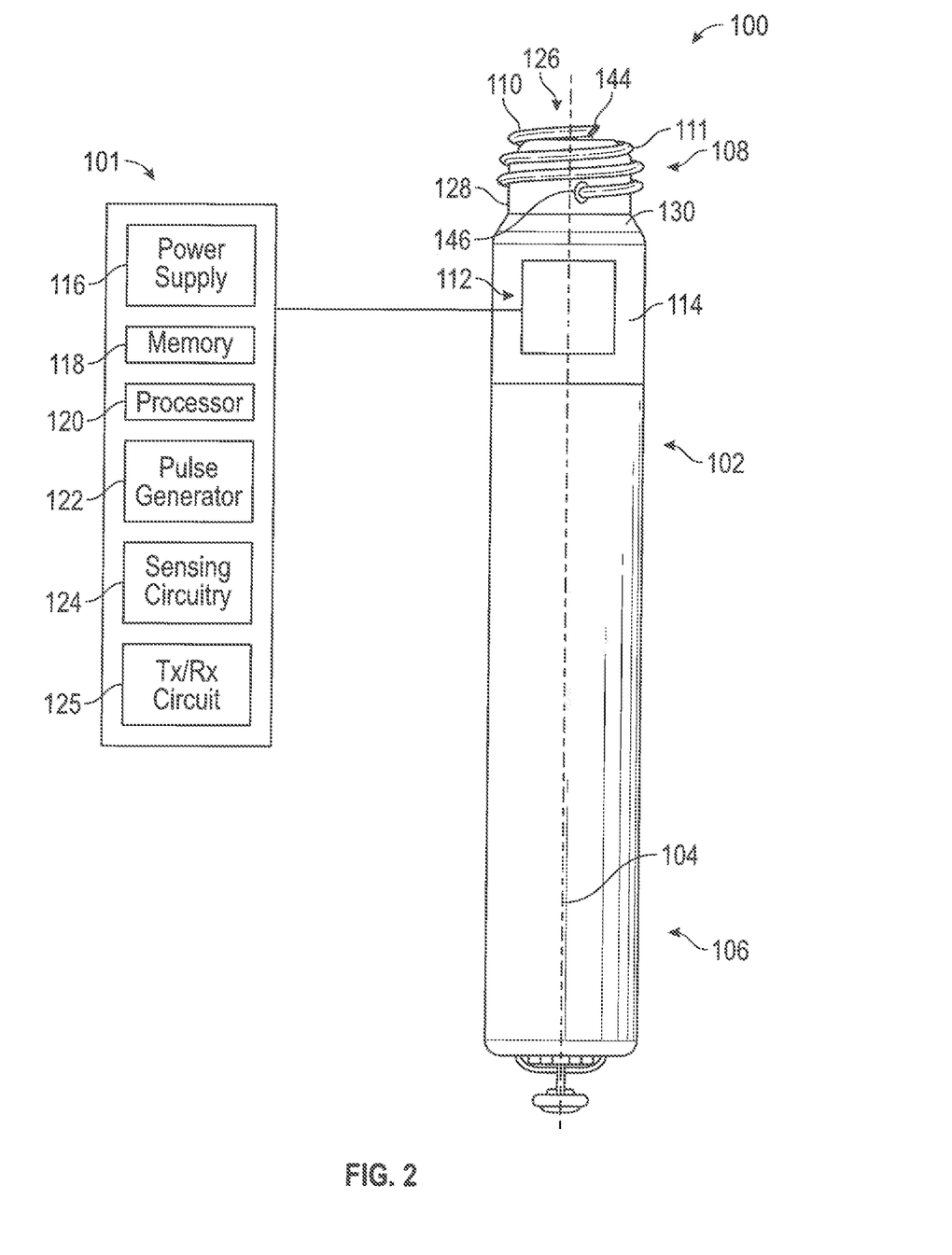
FIG. 2 illustrates a side view of the LIMD and a schematic representation of internal components according to an embodiment.

FIG. 2 illustrates a side view of the LIMD 100 and a schematic representation of a portion of the internal components according to an embodiment. The LIMD 100 includes a hermetic housing 102 that is elongated and extends along a longitudinal axis 104. The housing 102 can comprise a conductive, biocompatible, inert, and anodically safe material such as titanium, 316L stainless steel, or other similar materials. In alternate embodiments, the housing 102 can be cylindrically shaped, rectangular, spherical, or any other appropriate shapes. The housing 102 includes a proximate portion 106 and opposite distal portion 108 configured for mounting to tissue of an intra-cardiac wall within a chamber of the heart 10 with a fixation antenna 110, and an intermediate portion 112 extending between the proximate portion 106 and the distal portion 108.

The intermediate portion 112 includes a compartment 114 that contains the electronics circuit 101 for operation of the LIMD 100, including, for example, a power supply 116, a memory 118, one or more processors 120, a pulse generator 122, a sensing circuit 124, and a transceiver circuit 125. The electronics circuit 101 is configured to perform one or both of sensing and stimulation operations. The electronics circuit 101 may sense cardiac signals from one or more electrodes 126, such as in connection with monitoring cardiac activity and/or sensing cardiac signals to determine whether/when to deliver a pacing therapy. The electronics circuit 101 may also generate and deliver pacing signals to one or more electrodes 126.

More specifically, the sensing circuit 124 senses the cardiac signals, the processor 120 determines whether a pacing signal is warranted and if so, the pulse generator 122 generates and delivers the pacing signal to the electrode 126.

The transceiver ($T_X/R_X$) circuit 125 is configured to communicate wirelessly with an external device in accordance with a select protocol, such as a Bluetooth protocol, WiFi protocol, Bluetooth low energy (BLE) protocol, Medical Implant Communications Standard (MICS) protocol, and the like.

In accordance with embodiments herein, the transceiver circuit 125 is electrically coupled to the fixation mechanism 110 and the fixation mechanism 110 is configured to operate as an antenna for communication between the LIMD 100 and an external device.

Figure 3:
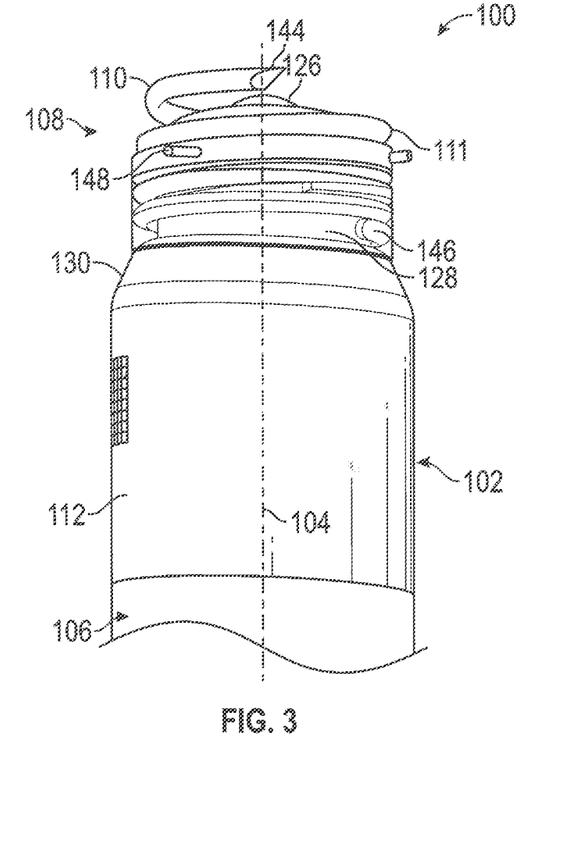
FIG. 3 illustrates an enlarged side view of a distal end of the LIMD pacemaker according to an embodiment.
Figure 4:
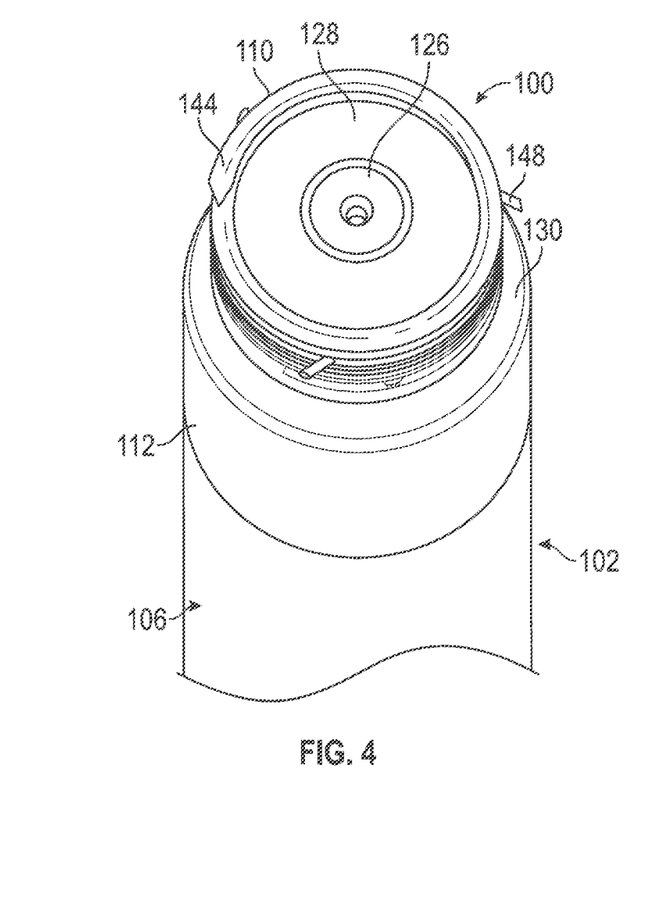
FIG. 4 illustrates an enlarged perspective view of the distal end of the LIMD according to an embodiment.

FIGS. 3-4 illustrate an enlarged side and top views of the distal portion 108 of the LIMD 100 according to an embodiment. A pacing electrode 126 is disposed on the distal portion 108 of the housing 102 with an insulative cap 128. The cap 128 electrically insulates the pacing electrode 126 from the proximate portion 106 of the housing 102. All or a portion of the proximate portion 106 of the housing 102 may be utilized as a separate electrode. Optionally, the LIMD 100 may include multiple sensing/pacing electrodes positioned at select points about the housing 102 (not shown). The electrodes may be located in various locations on the housing 102 based on the shape of the LIMD 100, the implant location, the intended use of the LIMD 100 and the like. For example, when separate housing portions are provided for the electronic components and the battery, one or more electrodes may be located on the housing portion that holds the battery. An insulative coating may be provided on a portion of the housing 102, such as between electrodes and can comprise materials such as PEEK, tecothane, silicone, polyurethane, parylene, or another biocompatible electrical insulator commonly used for implantable medical devices. In some embodiments, the housing 102 itself can comprise an insulator instead of a conductor, such as an alumina ceramic or other similar materials, and electrodes can be disposed upon the housing 102.

The pacing electrode 126 is configured for delivery of stimulation energy to a tissue of interest. As used herein, "tissue of interest" refers to intra-cardiac tissue that the LIMD 100 is configured to monitor and provide stimulation energy. In the illustrated embodiment, the LIMD 100 is configured for affixation directly to the tissue of interest, as described below. The pacing electrode 126 may be a cathode electrode that is actively fixated to the myocardium. The stimulation energy may be in the form of low-energy pacing pulses, higher-energy shocking pulses, or the like. When the distal portion 108 is mounted to the intra-cardiac tissue, the pacing electrode 126 is securely affixed to and engages the tissue of interest in order to deliver the stimulation energy directly thereto. In addition to delivering stimulation energy, in an alternative embodiment the pacing electrode 126 may be used to sense electrical activity from the tissue of interest. The pacing electrode 126 may be formed as a single conductive bulb or, alternatively, as a cone, a single wire, or the like.

The pacing electrode 126 can comprise a "button" or dome shape that protrudes slightly distally from the distal portion 108 of the LIMD 100. The dome shaped pacing electrode 126 can include a diameter of about 1.5-2.5 mm and can protrude distally from the end of the pacemaker approximately 0.05" to 0.3". The pacing electrode 126 is preferably an atraumatic surface, and can protrude from the distal portion 108 of the LIMD 100 to contact the tissue when the fixation antenna 110 is screwed into tissue.

The fixation antenna 110 includes a body 111 that extends between a distal end 144 and a proximal end 146. The fixation antenna 110 can comprise a helix that partially surrounds or rotates about the longitudinal axis 104 and the cap 128. The helix can comprise a constant diameter that is less than or equal to the outer diameter of the pacemaker housing 102. In one embodiment, the fixation antenna 110 comprises a diameter of less than 5 mm. In another embodiment, the fixation antenna 110 comprises a diameter of greater than 2.5 mm and less than 5 mm. In some embodiments, the helical fixation antenna 110 can have a wire diameter of 0.005" to 0.03" and a pitch of 0.5 mm to 1.5 mm. Each coil of the fixation antenna 110 includes a gap G that is large enough to prohibit contact and electrical shorts between the coils. Utilizing a fixation antenna 110 having a diameter up to the diameter of the housing 102 can increase the pull force required to remove the fixation antenna 110 from tissue, thereby decreasing the chances of the device coming dislodged from the heart 10. Furthermore, the increased diameter of the fixation antenna 110 can increase the surface area in contact with the endocardium layer of the heart 10, further improving the ability of the LIMD 100 to remain implanted in the patient.

The helical fixation antenna 110 can comprise a coil having less than five (5) full rotations from the distal end 144 of the fixation antenna 110 to the proximal end 146. For example, the distal end 144 of the fixation antenna 110 is approximately three (approximately 1,080 degrees) from the proximal end 116 of the fixation antenna 110. The cap 128 and fixation antenna 110 can have an outer diameter less than the outer diameter of the intermediate portion 112 and proximate portion 106 of the housing 102, so as to facilitate attachment of the fixation antenna 110. When the fixation antenna 110 is fully screwed into the cardiac tissue, the pacing electrode 126 of the LIMD 100 is in solid contact with the tissue.

Optionally, the fixation antenna 110 can include anti-rotation features 148 such as barbs or sutures to prevent counter rotation of the device once it has been screwed into tissue.

The helical fixation antenna 110, can enable insertion of the device endocardially or epicardially through a guiding catheter. A torqueable catheter can be used to rotate the housing 102 and force the fixation antenna 110 into heart tissue, thus affixing the fixation antenna 110 (and also the pacing electrode 126 in FIG. 1) into contact with stimulable tissue. The fixation antenna 110 may be coated partially or in full for electrical insulation, and a steroid-eluting matrix may be included on or near the device to minimize fibrotic reaction, as is known in conventional pacing electrode-leads.

The fixation antenna 110 operates as a monopole antenna. For example, the fixation antenna 110 may be formed as a wire antenna connected at the proximal end 146 to the feedthrough pin 134 and open at the distal end 144. RF signals are conducted from the transceiver circuit 125 through the feedthrough assembly 130, along the fixation antenna 110, toward the open distal end 144 where the signal radiates into space.

The length of the fixation antenna 110 is adjusted to tune the antenna characteristics to a desired frequency. The length of the fixation antenna 110 is directly related to a resonant frequency of operation, and thus the length can be adjusted to be longer or shorter depending on the communications protocol being used. For example, in certain applications, the fixation antenna 110 may be tuned to communicate at a select frequency of 400 MHz or 2.4 GHz. The fixation antenna 110 may be constructed to support communications in the frequency ranges associated with a Bluetooth protocol, a Wi-Fi protocol, Medical Implant Communications Standard (MICS), or various other wireless protocols.

As a further example, the body 111 of the fixation antenna 110 may be formed with a length based on a wavelength of a carrier frequency with an external device, such as a length that corresponds approximately to (or is greater than) a quarter multiple of the wavelength of the desired carrier frequency. For example, when the fixation antenna operates at the frequency of 2.4 GHz, the fixation antenna may be constructed with an overall length of approximately 31.25 mm. Optionally, the fixation antenna may be constructed to have a length corresponding to or greater than one half of the wavelength of the desired frequency. As a further example, the fixation antenna 110 may have a length that is equal to or greater than the wavelength of the desired frequency. For example, when utilizing the frequency of 2.4 GHz, the overall length may be approximately 62.5 mm, 93.75 mm, 125 mm, etc. The overall length of the fixation antenna 110 is measured from the distal end 144 to the proximal end 146. The pitch and the height of the helix can also vary to accommodate communication requirements or standards. In addition, the insertion of a portion of the fixation antenna 110 in heart tissue helps maintain the impedance generally constant. Generally, antenna impedance is more stable when the antenna is inserted into heart tissue as opposed to blood. For example, there is less movement of the antenna when anchored into heart tissue. As a result, the antenna maintains a constant contact with the heart tissue. In addition, heart tissue has known and generally consistent material properties. In contrast, the material properties of blood can vary.

The fixation antenna 110 comprises a generally rigid material with low deflection characteristics, such as a shore hardness ranging between 35-55 Rockwell C HRC. For example, the fixation antenna 110 can be formed of a material having a deflection $DEF = LEN_{REST}/LEN_{EXTEND}$ that is no more than 50%, wherein $LEN_{REST}$, and $LEN_{EXTEND}$ are described above in the terms section. The deflection of the fixation antenna 110 from the initial to final length is typically no more than 50%, and preferable 5%-40%.

LIMD Circuits

Figure 5:
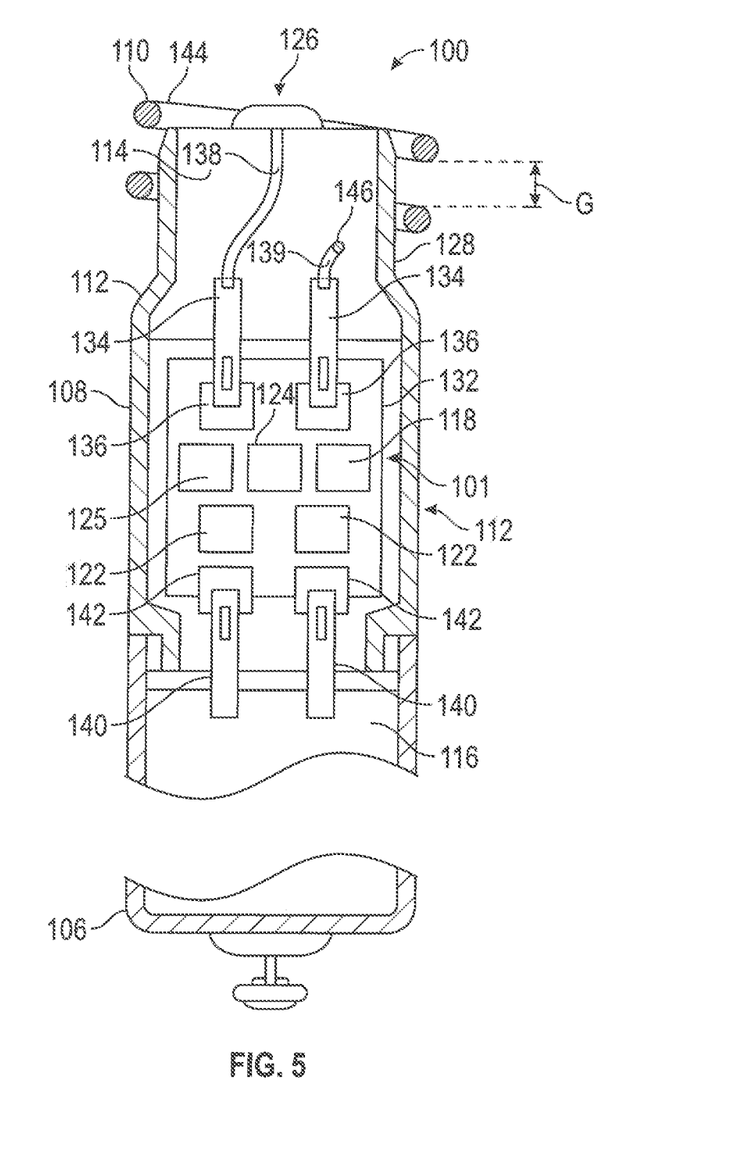
FIG. 5 illustrates a partial cross-section view of the LIMD according to an embodiment.

FIG. 5 illustrates a partial cross-section view of the LIMD 100 according to an embodiment. The housing 102 includes a cap 128 that is mounted to a feedthrough assembly 130. The pacing electrode 126 is provided on the cap 128. The pacing electrode 126 is electrically connected to the electronics circuits 101. The electronics circuits 101 is mounted to one or more circuit boards 132 that are coupled to feedthrough pins 134 at pads 136. The feedthrough pins 134 extend through the feedthrough assembly 130 and are electrically coupled with the pacing electrode 126 and fixation antenna 110 through respective wires 138, 139 and suitable connection, such as welding, soldering, or connector, with feedthrough pins 134. The feedthrough pins 134 may include a dielectric material (not shown) that separates the inner and outer portions of the pins 134. Conductors 140 connect to the circuit board 132 with pads 142 and electrically connect to the power supply 116, such as a battery. Optionally, a ground connection (not shown) can also be maintained between the feedthrough assembly 130 and the circuit board 132. It is understood that the example of FIG. 5 represents one exemplary construction, while LIMDs may be constructed with numerous alternative shapes and combinations of components therein.

As mentioned above, the housing 102 includes a power supply 116 and various electronics circuits 101 that receive electrical current from the power supply 116. The electronics circuits 101 provide the functionality of the LIMD 100, such as controlling the stimulation energy delivered to the pacing electrode 126 and sensing the depolarization along the tissue of interest in response to a pacing pulse or to an intrinsic heartbeat. The power supply 116 may be a battery that has a fixed amount of charge at full capacity. The power supply 116 may be rechargeable in some embodiments, and may not be rechargeable in other embodiments.

The illustration in FIG. 2 is intended as an overview of the electronic components only, and the electronic components according to an embodiment of the LIMD 100 are described in more detail below with reference to FIG. 5. The pulse generator 122 provides stimulation energy to the pacing electrode 126 which is delivered to the tissue of interest that the pacing electrode 126 engages. The pulse generator 122 includes circuitry to control the output of stimulation energy directed to the pacing electrode 126. For example, the pulse generator 122 produces lower energy pulses for pacing and higher energy pulses for shocking.

The processor 120 is a controller that controls the flow of charge between the power supply 116, the electronics circuits 101 (such as the pulse generator 122 and the sensing circuit 124), and the electrodes (such as pacing electrode 126). For example, the processor 120 controls the timing and intensity or magnitude of the stimulation pulses. If multiple electrodes are used to deliver stimulation energy to the intra-cardiac tissue, the processor 120 may synchronize the delivery of the pulses. The processor 120 is communicatively coupled to the pulse generator 122, the sensing circuit 124, the memory 118, and the power supply 116. The processor 120 controls the flow of charge based on input information received from the sensing circuit 124. The processor 120 also functions based on instructions stored locally in the memory 118. The memory 118 is a non-transitory tangible computer readable storage medium. The memory 118 stores programmable and executable instructions for the processor 120. The processor 120 is responsive to the programmable instructions to control operation of the LIMD 100. The memory 118 may also store data. Some of the data may be stored prior to completing assembly of the LIMD 100, while other data may be stored during use of the implanted LIMD 100. For example, the memory 118 may be used to store data on intrinsic electrical activity within the heart as monitored by the sensing circuit 124, data on the number, time, and/or magnitude of pacing pulses generated by the pulse generator 122, or the like.

The sensing circuit 124 is configured to monitor intrinsic electrical activity within the heart. The sensing circuit 124 is communicatively coupled to the pacing electrode 126 which doubles as a sensing electrode, such that the pacing electrode 126 is used to deliver stimulation pulses and, in-between pulses, monitors the electrical activity within the tissue of interest for the sensing circuit 124. In an alternative embodiment, the sensing electrode is different from the pacing electrode 126, because the sensing electrode does not deliver stimulation energy to the intra-cardiac tissue.

Figure 6:
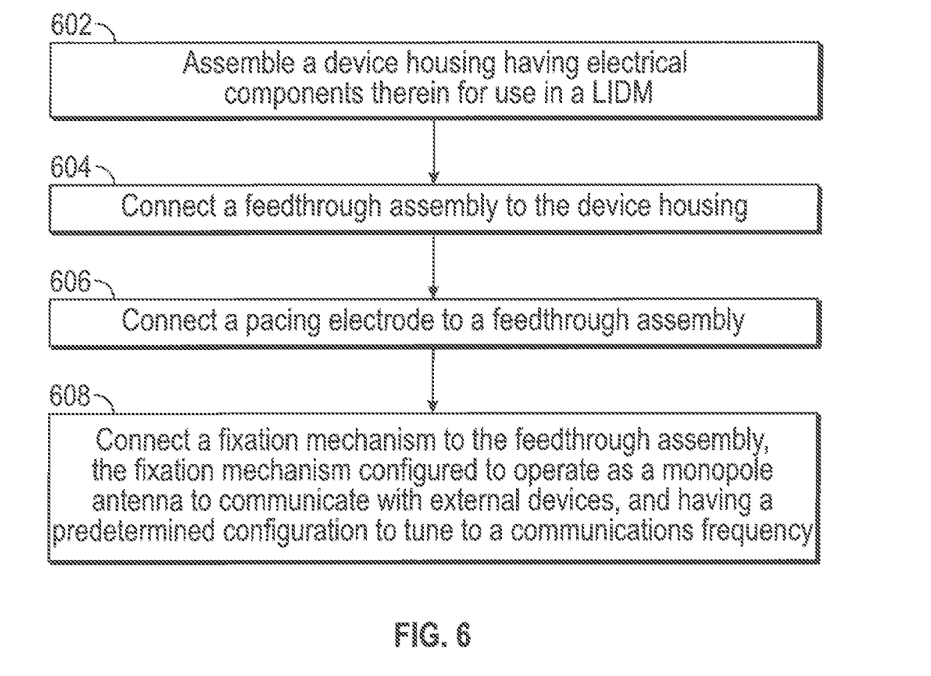
FIG. 6 illustrates a method for providing the LIMD according to an embodiment.

FIG. 6 illustrates a method for providing an implantable cardiac monitoring device in accordance with embodiments herein. At 602, the process includes assembling a device housing having electronic components therein. Examples of the various electronic components are described herein. The electronic components may include sensing circuitry to sense cardiac signals of interest, one or more processors to perform monitoring operations, transceiver circuitry to communicate with external devices and other components as described herein and/or understood by one of ordinary skill in the art. The memory, processors, and other electronic components are within a housing formed of a biocompatible material.

At 604, the process includes connecting a feedthrough assembly to the device housing. The housing includes a feedthrough opening at one end and a battery attachment at the opposite end. A hermetically sealed battery is welded to the battery attachment surface, and a feedthrough is welded to the feedthrough opening, thereby hermetically sealing the interior of the housing.

At 606 a pacing electrode includes connecting a pacing electrode to the feedthrough assembly. The pacing electrode 126 is configured for delivery of stimulation energy to a tissue of interest.

At 608, a fixation antenna is connected to the feedthrough assembly to electrical components. The fixation antenna operates as a monopole antenna for communication with external devices. The fixation antenna can have a predetermined configuration, such as a predetermined length, pitch, and shape to tune the antenna to a communications frequency or standard. The fixation antenna includes an overall length extending from a proximal end that is connected to feedthrough pins of the feedthrough assembly, to an open distal end, for communication of RF signals.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

The processors/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the processors/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The processors/applications herein may execute a set of instructions that are stored in one or more storage elements, in order to process data. The storage elements may also store data or other information as desired or needed. The storage element may be in the form of an information source or a physical memory element within the processors/controllers herein. The set of instructions may include various commands that instruct the processors/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A leadless implantable medical device, comprising:
a housing;
an electrode disposed on the housing;
an electronics circuit disposed in the housing, the electronics circuit configured to at least i) sense cardiac signals from the electrode or ii) generate and deliver pacing signals to the electrode;
a transceiver circuit disposed in the housing, the transceiver circuit configured to communicate wirelessly with an external device; and
a fixation antenna electrically separate from the electrode and partially disposed on a distal portion of the housing, the fixation antenna being configured to penetrate cardiac tissue to affix the leadless implantable device to the cardiac tissue, the fixation antenna being electrically coupled to the transceiver circuit and configured to operate as an antenna for communication between the transceiver circuit and the external device, wherein the housing includes a feedthrough, the fixation antenna includes a proximal end connected through the feedthrough to the transceiver circuit, the fixation antenna including a distal end that is electrically open.

2. The device of claim 1, wherein the fixation antenna is configured to operate sa monopole antenna for communication between the transceiver circuit and the external device.

3. The device of claim 1, wherein the fixation antenna includes a body that extends between the proximal and distal ends, the body having a length defined based on a wavelength of a carrier frequency for communication with the external device.

4. The device of claim 3, wherein the lent the of the body is a quarter multiple of the wavelength of the carrier frequency.

5. The device of claim 1, wherein the transceiver circuit and fixation antenna are configured to communicate in accordance with at least one of a MICS protocol, a BLE protocol, a WiFi protocol, or a Bluetooth protocol.

6. The device of claim 1, wherein the fixation antenna has a body that is shaped as one of a helix, hook or straight needle.

7. The device of claim 1, wherein the housing is elongated and extends along a longitudinal axis, the fixation antenna is wound in a helix about the longitudinal axis, the fixation antenna formed of a material having a deflection $DEF=LEN_{REST}/LEN_{EXTEND}$ that is no more than 50%, wherein $LEN_{REST}$ represents a rest length of the fixation antenna along the longitudinal axis when in a rest non-extended state, and $LEN_{EXTEND}$ represents an extended length of the fixation antenna along the longitudinal axis when deflected to a fully extended state.

8. The device of claim 1 wherein the transceiver circuit and fixation antenna are configured to communicate at a frequency of at least one of 400 MHz or 2.46 Hz.

9. The device of claim 1 wherein the fixation antenna has a diameter between 2.5 mm and 5 mm.

* * * * *